United States Patent
Riebel et al.

(10) Patent No.: US 7,642,436 B2
(45) Date of Patent: Jan. 5, 2010

(54) PETUNIA MUTANT ALLELE

(75) Inventors: Melvin Riebel, Le Sueur, MN (US); Jianping Ren, Geneva, IL (US); Alan D. Blowers, Elburn, IL (US)

(73) Assignee: Ball Horticultural Company, West Chicago, IL (US)

( * ) Notice: Subject to any disclaimer, the term of this patent is extended or adjusted under 35 U.S.C. 154(b) by 104 days.

(21) Appl. No.: 11/734,924

(22) Filed: Apr. 13, 2007

(65) Prior Publication Data

US 2008/0256658 A1    Oct. 16, 2008

(51) Int. Cl.
*A01H 4/00* (2006.01)
*A01H 5/00* (2006.01)
*A01H 5/10* (2006.01)
*C12N 15/05* (2006.01)

(52) U.S. Cl. .............. 800/323.1; 800/266; 800/270; 800/298; 435/410; 435/421; 435/430; 435/430.1

(58) Field of Classification Search .......... None
See application file for complete search history.

(56) References Cited

U.S. PATENT DOCUMENTS

PP14,273 P2 *  11/2003  Hanes
PP16,358 P3 *   3/2006  Iwaki et al.

FOREIGN PATENT DOCUMENTS

JP    15568    3/2005

OTHER PUBLICATIONS

Angenent, Gerco C., et al., 1994. Co-suppression of the petunia homeotic gene fbp2 affects the identity of the generative meristem. The Plant Journal 5(1):33-34.

* cited by examiner

*Primary Examiner*—Russell Kallis
(74) *Attorney, Agent, or Firm*—Jondle & Associates, P.C.

(57) ABSTRACT

The present invention relates to a *petunia* plant, seed, variety and hybrid. More specifically, the invention relates to a *petunia* plant having an allele which results in a *petunia* plant with altered flower color and/or altered flower color pattern. The invention also relates to crossing *petunia* plants containing the allele with *petunia* or *Calibrachoa* plants lacking the allele to produce novel types of *petunia* and *Calibrachoa-petunia* inter-generic hybrid plants.

24 Claims, No Drawings

PETUNIA MUTANT ALLELE

BACKGROUND OF THE INVENTION

The present invention relates to an allele of *petunia* designated green corolla 1-1 (gc1-1), which results in altered flower color and/or flower color pattern. The present invention also relates to a *petunia* seed, a *petunia* plant and parts of a *petunia* plant, a *petunia* variety and a *petunia* hybrid which comprise the mutant allele. In addition, the present invention is directed to transferring the gc1-1 allele in the *petunia* plant to other *petunia* or *calibrachoa* varieties and species and is useful for producing new types and varieties of *petunia*.

The geographic origin of *Petunia* is South America, where various species have been found in Argentina, Brazil, Bolivia, Paraguay, and Uruguay. The primary locations for species diversity are mostly limited to the three Brazilian provinces of Parana, Santa Catarina, and Rio Grande do Sul particularly along river banks and isolated areas (Sink ed., *Petunia: Monographs on Theoretical and Applied Genetics*, Springer-Verlag: Berlin, Germany (1984)).

Jussieu first established the genus *Petunia* in 1803. Since that time, the *Petunia* genus has undergone constant restructuring and is still somewhat unsettled today. Fries wrote the first *Petunia* monograph in 1911 where he proposed the division of the genus into two distinct subgenera, *Pseudonicotiana* and *Eupetunia*. Species in the subgenera of *Pseudonicotiana* had long, narrow corolla tubes, while species in the subgenera *Eupetunia* had short, wide corolla tubes (Sink ed., *Petunia: Monographs on Theoretical and Applied Genetics*, Springer-Verlag: Berlin, Germany (1984)).

The cultivated garden *petunia*, *Petunia×hybrida*, is not a true species but actually a complex interspecific hybrid of two or more *Petunia* species. In earlier literature, many taxonomists and scientists suggested that as many as five different species including *P. axillaris, P. integrifolia, P. parodii, P. inflata*, and *P. violacea* all contributed to the origin of *P.×hybrida*. Even today there is still disagreement over whether many species of *Petunia*, like *P. inflata, P. occidentalis*, and *P. parodii*, are actually true species or are subspecies of either *P. integrifolia* or *P. axillaris* (Wijsman, *Acta Bot. Neerl.* 31: 477-490 (1982), Griesbach and Beck, *HortScience* 35(7): 1347-1349 (2000) and Mishiba et al., *Annals of Botany* 85: 665-673 (2000)).

During the 1980s and 1990, H. J. Wijsman published a series of articles regarding the ancestry of *P.×hybrida* and the inter-relationship of several species classified as *Petunia*. These studies discovered that *P.×hybrida* and its ancestral species, *P. nyctaginiflora* (=*P. axillaris*) and *P. violacea* (=*P. integrifolia*), possessed 14 pairs of chromosomes while several other species, including *P. parviflora*, possessed 18 pairs of chromosomes. Since *P. parviflora* was the lectotype species for the *Petunia* genus, Wijsman and J. H. de Jong proposed transferring the 14-chromosome species to the genus *Stimoryne*. Horticulturists opposed reclassifying the garden *petunia* and in 1986, Wijsman proposed the alternative of making *P. nyctaginiflora* the lectotype species for *Petunia* and transferring the 18-chromosome species to another genus. The I. N. G. Committee adopted this proposal. By 1990 Wijsman had transferred several species, including *P. parviflora* (=*C. parviflora*) to *Calibrachoa*, originally established by Llave and Lexarza in 1825. *Calibrachoa parviflora* (=*C. mexicana* Llave & Lexarza) is now the type species for the genus *Calibrachoa*.

In the horticultural industry, *petunias* are found in a variety of forms for landscape, home garden, and container use. Marketable series have been developed for upright, spreading and semi-trailing to trailing growth habits. Leaf colors range from light to dark green and can have variegated types. Flower colors range from white, yellow, and shades of pink, rose, salmon, red, burgundy, and purple with mixtures found in a variety of patterns. Flower color patterns include morn, having a throat color that extends to the petal area, picotee, having an outer margin of another color, star, having two colors one of which forms a star, veined, having pronounced venation of a darker color. Flower types include both double and single. Single and double flower *petunias* are further categorized as *grandiflora* or *multiflora* types. *Grandiflora petunia* plants typically having large flowers with wide sepals, thick filaments, and large stigmas. It is inherited as a single dominant gene. *Multiflora petunia* plants typically having small flowers with narrow sepals, thin filaments, and small stigmas. It inherited as a single recessive gene. Although *multiflora*-type flowers are smaller than *grandiflora* type, the *multiflora* types are further divided into small and large flower sizes.

There are numerous steps in the development of any novel, desirable plant germplasm. Plant breeding begins with the analysis and definition of problems and weaknesses of the current germplasm, the establishment of program goals, and the definition of specific breeding objectives. The next step is selection of germplasm that possess the traits to meet the program goals. The goal is to combine in a single variety or hybrid an improved combination of desirable traits from the parental germplasm. These important traits may include flower color and size, number of flowers, improved plant vigor, resistance to diseases and insects, and tolerance to drought and heat.

Choice of breeding or selection methods depends on the mode of plant reproduction, the heritability of the trait(s) being improved, and the type of cultivar used commercially (e.g., $F_1$ hybrid cultivar, pureline cultivar, etc.). For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, and recurrent selection.

The complexity of inheritance influences choice of the breeding method. Backcross breeding is used to transfer one or a few favorable genes for a highly heritable trait into a desirable cultivar. This approach has been used extensively for breeding disease-resistant cultivars. Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

Each breeding program should include a periodic, objective evaluation of the efficiency of the breeding procedure. Evaluation criteria vary depending on the goal and objectives, but should include gain from selection per year based on comparisons to an appropriate standard, overall value of the advanced breeding lines, and number of successful cultivars produced per unit of input (e.g., per year, per dollar expended, etc.).

Promising advanced breeding lines are thoroughly tested and compared to appropriate standards in environments representative of the commercial target area(s). The best lines are candidates for new commercial cultivars; those still deficient in a few traits are used as parents to produce new populations for further selection.

These processes, which lead to the final step of marketing and distribution, usually take from eight to 12 years from the time the first cross is made. Therefore, development of new cultivars is a time-consuming process that requires precise forward planning, efficient use of resources, and a minimum of changes in direction.

A most difficult task is the identification of individuals that are genetically superior, because for most traits the true genotypic value is masked by other confounding plant traits or environmental factors. One method of identifying a superior plant is to observe its performance relative to other experimental plants and to a widely grown standard cultivar. If a single observation is inconclusive, replicated observations provide a better estimate of its genetic worth.

The goal of *petunia* plant breeding is to develop new, unique and superior *petunia* plants. The breeder initially selects and crosses two or more parental lines, followed by repeated selfing and selection, producing many new genetic combinations. The breeder can theoretically generate billions of different genetic combinations via crossing, selfing and mutations. The breeder has no direct control at the cellular level. Therefore, two breeders will never develop the same line, or even very similar lines, having the same *petunia* traits.

With each cross, the plant breeder selects the germplasm to advance to the next generation. This germplasm is grown under unique and different geographical, climatic and soil conditions, and further selections are then made, during and at the end of the growing season. The varieties which are developed are unpredictable. This unpredictability is because the breeder's selection occurs in unique environments, with no control at the DNA level (using conventional breeding procedures), and with millions of different possible genetic combinations being generated. A breeder of ordinary skill in the art cannot predict the final resulting lines he develops, except possibly in a very gross and general fashion. This unpredictability results in the expenditure of large research funds to develop a superior new *petunia* variety.

Each year, the plant breeder selects the germplasm to advance to the next generation. This germplasm is grown under unique and different geographical, climatic and soil conditions, and further selections are then made, during and at the end of the growing season. The varieties which are developed are unpredictable. This unpredictability is because the breeder's selection occurs in unique environments, with no control at the DNA level (using conventional breeding procedures), and with millions of different possible genetic combinations being generated. A breeder of ordinary skill in the art cannot predict the final resulting lines he develops, except possibly in a very gross and general fashion. The same breeder cannot produce the same line twice by using the exact same original parents and the same selection techniques. This unpredictability results in the expenditure of large research monies to develop superior new *petunia* varieties.

Mass and recurrent selections can be used to improve populations of either self- or cross-pollinating crops. A genetically variable population of heterozygous individuals is either identified or created by intercrossing several different parents. The best plants are selected based on individual superiority, outstanding progeny, or excellent combining ability. The selected plants are intercrossed to produce a new population in which further cycles of selection are continued.

Backcross breeding has been used to transfer genes for a simply inherited, highly heritable trait into a desirable homozygous cultivar or inbred line which is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent.

The development of commercial *petunia* hybrids typically requires the development of homozygous inbred lines, the crossing of these lines, and the evaluation of the crosses. Pedigree breeding and recurrent selection breeding methods are used to develop inbred lines from breeding populations. Breeding programs combine desirable traits from two or more inbred lines or various broad-based sources into breeding pools from which inbred lines are developed by selfing and selection of desired phenotypes. The new inbreds are crossed with other inbred lines and the hybrids from these crosses are evaluated to determine which have commercial potential.

Commercially available *petunia* varieties are primarily $F_1$ hybrids. In $F_1$ hybrid varieties, pollen from an inbred "male" line is used to pollinate an inbred, but genetically different "female" line. The resulting $F_1$ hybrids are both phenotypically highly uniform and vigorous. In addition to this hybrid vigor, hybrids also offer opportunities for the rapid and controlled deployment of dominant genes. A homozygous dominant gene in one parent of a hybrid will result in all $F_1$ hybrids expressing the dominant gene phenotype. Within the seed trade industry, $F_1$ hybrids command the preeminent role because of their superior vigor, uniformity and performance.

Descriptions of other breeding methods that are commonly used for different traits and crops can be found in one of several reference books (e.g., Principles of Plant Breeding, John Wiley and Son, pp. 115-161, 1960; Allard, 1960; Simmonds, 1979; Sneep et al., 1979; Fehr, 1987).

The foregoing examples of the related art and limitations related therewith are intended to be illustrative and not exclusive. Other limitations of the related art will become apparent to those of skill in the art upon a reading of the specification.

SUMMARY OF THE INVENTION

The foregoing examples of the related art and limitations related therewith are intended to be illustrative and not exclusive. Other limitations of the related art will become apparent to those of skill in the art upon a reading of the specification.

The present invention provides a new allele designated gc1-1 derived from *Petunia* that is phenotypically expressed by the production of altered flower color and/or flower color pattern when present in either the heterozygous or homozygous state. This mutant allele has been determined to be a single dominant or partially dominant gene. The invention further provides plants, seeds, and other plant parts such as pollen and ovules containing the mutant allele.

The invention also provides methods for introducing the allele of the present invention into plants by crossing a plant which lacks the mutant allele with a plant that has the allele, selfing the resulting generations and then selecting the plants exhibiting altered flower color.

In another aspect, the invention provides a method for producing a hybrid *Petunia* seed comprising crossing a first plant parent with a second plant parent and harvesting the resultant hybrid *Petunia* seed, wherein either one or both parents contain gc1-1, the mutant allele. The hybrid seeds, plant and parts thereof produced by such method are also part of the invention.

In another aspect, the invention provides a method for producing an inter-generic hybrid *Calibrachoa-petunia* plant comprising crossing a first *petunia* plant parent with a second *calibrachoa* plant parent and harvesting the resultant hybrid

*Calibrachoa-petunia* plant, wherein one or both parents contain the mutant allele. The hybrid plant and parts thereof produced by such method are also part of the invention.

Another aspect of the invention relates to any *petunia* seed or plant having the mutant allele gc1-1.

Another aspect of the invention relates to any *Calibrachoa-petunia* hybrid seed or plant having the mutant allele gc1-1.

In another aspect, the present invention provides regenerable cells for use in tissue culture. The tissue culture will preferably be capable of regenerating plants having the physiological and morphological characteristics of the foregoing *petunia* or *calibrachoa-petunia* hybrid plant, and of regenerating plants having substantially the same genotype as the foregoing starting plant. Preferably, the regenerable cells in such tissue cultures will be embryos, protoplasts, meristematic cells, callus, pollen, leaves, anthers, pistils, stems, petioles, roots, root tips, seeds, flowers, cotyledons, hypocotyls or the like. Still further, the present invention provides *petunia* plants regenerated from the tissue cultures of the invention.

In addition to the exemplary aspects and embodiments described above, further aspects and embodiments will become apparent by study of the following descriptions.

DEFINITIONS

In the description and tables which follow, a number of terms are used. In order to provide a clear and consistent understanding of the specification and claims, including the scope to be given such terms, the following definitions are provided:

Allele. "Allele" is any of one or more alternative forms of a gene, all of which alleles relate to one trait or characteristic. In a diploid cell or organism, the two alleles of a given gene occupy corresponding loci on a pair of homologous chromosomes.

Diploid plants. "Diploid plants" means plants or transplants derived from planting diploid seeds or from micro propagation.

Essentially all the physiological and morphological characteristics. A plant having "essentially all the physiological and morphological characteristics" means a plant having the physiological and morphological characteristics, except for the characteristics derived from the converted gene.

*Grandiflora petunia* (gf). A "*grandiflora petunia*" is a *petunia* plant typically having large flowers with wide sepals, thick filaments, and large stigmas. The *grandiflora* characteristic is inherited as a single dominant gene.

*Multiflora petunia* (mf). A "*multiflora petunia*" is a *petunia* plant typically having small flowers with narrow sepals, thin filaments, and small stigmas. The *multiflora* characteristic is inherited as a single recessive gene.

Plant. "Plant" includes plant cells, plant protoplasts, plant cells of tissue culture from which *petunia* plants can be regenerated, plant calli, plant clumps and plant cells that are intact in plants or parts of plants such as pollen, flowers, pistils, anthers, seeds, leaves, stems, and the like.

Quantitative Trait Loci (QTL). "Quantitative trait loci (QTL)" refer to genetic loci that control to some degree numerically representable traits that are usually continuously distributed.

Regeneration. "Regeneration" refers to the development of a plant from tissue culture.

Single gene converted (conversion). "Single gene converted" (or conversion) plant refers to plants which are developed by a plant breeding technique called backcrossing wherein essentially all of the desired morphological and physiological characteristics of an inbred are recovered in addition to the single gene transferred into the inbred via the backcrossing technique or via genetic engineering.

DETAILED DESCRIPTION OF THE INVENTION

The present invention relates to a new allele designated "gc1-1" in the genus *Petunia* that is phenotypically expressed in altered flower color and/or flower color pattern. The present invention also relates to a *petunia* seed, a *petunia* plant and plant parts which comprise the new gc1-1 allele. The present invention also relates to a *calibrachoa-petunia* hybrid embryo, a *calibrachoa-petunia* inter-generic hybrid plant and plant parts which comprise the new gc1-1 allele. The present invention also relates to a method of producing the disclosed *petunia* and *calibrachoa-petunia* hybrid plants and seeds.

The mutant allele of the present invention can be introgressed into any *petunia* type and into any *calibrachoa* type. The allele of the present invention is readily transferred between a *petunia* plant containing the allele and into *petunia* and *calibrachoa* plants lacking the allele. The allele and the methods of the present invention can be used to modify the corolla color of all *Petunia* varieties and *Calibrachoa* varieties for commercial production. Generally, the methods involve controlled bud pollination or ovule culture. The crosses can be performed using either parent as the pollen parent.

A plant of the present invention can be obtained by crossing a plant either heterozygous or homozygous for the claimed mutant allele with any *petunia* or *calibrachoa* variety lacking the allele. The plant containing the allele can be any *Petunia* or *Calibrachoa* variety including a variety in which the factor has been previously genetically fixed. The trait may then be transmitted by sexual crossing to other varieties if desired.

Other breeding schemes can be used to introduce the gc1-1 allele into the desired variety. The particular scheme used is not critical to the invention, so long as the allele is stably incorporated into the genome of the variety. For example, a marker gene can be used. A nucleic acid probe which hybridizes to the marker gene can be used to identify the desired plants in the $F_1$ generation.

The gc1-1 allele will advantageously be introduced into varieties that contain other desirable genetic traits such as resistance to disease or pests, drought tolerance, double flowers and the like.

The *petunia* mutant of the present invention was an unexpected result that arose from a spontaneous mutation in a 'Supercascade White' commercial $F_1$ hybrid *petunia* population in May 2003. While the mutant plant was the result of a spontaneous mutation, it is believed that the mutation could also be created using a mutagenic agent. Substantially any kind of mutagen can be used to produce a mutated plant. Mutagenic agents useful for altering plants are well known in the art, as are methods of using such agents. Exemplary chemical mutagens include nitrosomethylurea (NMU), ethyl methanesulfonate (EMS), methyl methanesulfonate (MMS), diethyl sulfate, nitrosoguanidine (NG), and ethylnitrosourea (ENU). Irradiation is also a useful mutagenic agent.

The *petunia* mutant allele of the present invention was crossed into other *petunia* lines. A series of *petunia* plants expressing the mutant trait was produced. Self seed from this series of plants yielded plants which all had altered flower color and some had altered flower color pattern. The mutant allele does not limit seed yield. Seed production is indistinguishable from standard *petunia* breeding. Thousands of seeds have been developed using *petunia* plants expressing the mutant trait.

The invention also relates to methods for producing a *petunia* plant or a *calibrachoa* plant containing in its genetic material one or more transgenes and to the transgenic *petunia* plant or *calibrachoa* plant produced by that method. Preferably the transgene is mutant allele gc1-1 or cDNA of the mutant allele gc1-1.

The invention further provides methods for developing *petunia* plants in a plant breeding program using plant breeding techniques including parental selection and hybrid development, recurrent selection, backcrossing, pedigree breeding, restriction fragment length polymorphism enhanced selection, genetic marker enhanced selection and transformation. Seeds, *petunia* plants, and parts thereof produced by such breeding methods are also part of the invention.

The invention further provides methods for developing *calibrachoa-petunia* inter-generic hybrid plants in a plant breeding program using plant breeding techniques including parental selection and hybrid development, recurrent selection, backcrossing, pedigree breeding, restriction fragment length polymorphism enhanced selection, genetic marker enhanced selection and transformation. Embryos, *calibrachoa-petunia* hybrid plants, and parts thereof produced by such breeding methods are also part of the invention.

The present invention is directed to developing unique plants of the *Petunia* and *Calibrachoa-Petunia* hybrid species. A transferable allele, designated gc1-1, which conveys the altered flower color and altered flower color pattern characteristic has been isolated and incorporated into other genetic backgrounds. The allele of the instant invention has also been expressed in many different genetic backgrounds of *petunia*. The present invention is also directed to developing unique plants of the *Calibrachoa-Petunia* inter-generic hybrid species.

EXAMPLES

The following examples are provided to further illustrate the present invention and are not intended to limit the invention beyond the limitations set forth in the appended claims.

Example 1

Development of the Original Mutant Plant

The present invention arose from a spontaneous mutation in a Supercascade White commercial $F_1$ *petunia* population in May 2003. The mutant *petunia* plant designated 2171-1 and containing the mutant allele designated gc1-1 is characterized by a unique green flower color never before observed in *petunia*. Of particular interest is the unexpected and diverse range of colors never before observed in *petunia* that were expressed in the progeny when the mutant of the present invention was crossed with other *petunias* having different genetic backgrounds. The unique colors developed from this new gc1-1 mutation include but are not limited to lemon green, lemon yellow, dark yellow, orange yellow, peach, pinkish yellow, coral rose, greenish black, black, terracotta, antique shades of rose, burgundy, dark purple velvet, red with yellow star pattern, and burgundy with yellow star pattern. Colors were observed as solids and patterns including an unexpected splash pattern of an irregular mixture of two colors.

The single mutant plant, 2171-1 containing the mutant allele gc1-1 of the present invention, was self-pollinated and the progeny were sown in 2003. The $F_2$ plants segregated into *grandiflora* to *multiflora* and green- to white-flowered plants in a 3:1 ratio, indicating that the original mutant plant was a heterozygous *grandiflora* plant with dominant green flower color. This indicates that gc1-1 is a dominant allele. In later studies, the gc1-1 allele was found to be partially dominant in certain genetic backgrounds. The green color was not always completely expressed in $F_1$ or later generation plants when crossed with different breeding lines. In most cases, the green color was partially expressed resulting in unexpected color shades or splash patterns.

Example 2

Development of Two Homozygous Mutant Inbred Lines

The single mutant plant designated 2171-1 and containing the mutant allele gc1-1 of the present invention was self-pollinated and the progeny were sown in 2003. After several generations of self-pollination and selection between 2003 and 2005, two homozygous inbred mutant *petunia* lines with green flowers were produced. The first homozygous inbred mutant line consisted of plants with large green *grandiflora* flowers and a well-branched floriferous plant habit and was designated 2171-1-3-3-1. The second homozygous inbred mutant line consisted of plants with regular-sized green *multiflora* flowers and a well-branched floriferous plant habit and was designated 2171-1-1-5-2.

Example 3

Introgression of Mutant Allele gc1-1 into *Petunia* to Produce Novel Flower Color *Grandiflora Petunia* Hybrids The mutant plant 2171-1 containing the mutant allele gc1-1 of the present invention was also crossed with different *petunia* genetic backgrounds. Crosses were done by controlled bud pollination. The progeny seeds were sown and grown under controlled greenhouse conditions. Desirable plants were selected and self-pollinated or re-crossed with chosen breeding lines. Many plants with novel colors were derived from these crosses either in the first generation populations or the following generation populations.

In 2005, the inbred *grandiflora* line 2171-1-3-3-1 and the inbred *multiflora* line 2171-1-1-5-2, both containing the mutant allele gc1-1 of the present invention, described in Example 2 above were crossed as either the male or female parent with PanAmerican seed proprietary breeding lines to create several *grandiflora* hybrids having novel flower colors. Some examples are listed in Table 1 below.

As shown in Table 1, column 1 shows the number assigned to each hybrid, column 2 shows the type of hybrid, *grandiflora* (gf), column 3 shows the flower color of the hybrid, column 4 shows the number assigned to the female parent of the hybrid, column 5 shows the plant type of the female parent of the hybrid either *grandiflora* (gf) of *multiflora* (mf), column 6 shows the flower color of the female parent of the hybrid, column 7 shows the number assigned to the male parent of the hybrid, column 8 shows the plant type of the male parent of the hybrid (gf or mf) and column 9 shows the flower color of the male parent of the hybrid. The asterisk next to the number of the female parent or male parent of the hybrid indicates that particular parent contains the gc1-1 allele.

TABLE 1

Grandiflora *petunia* hybrids

| Hybrid Number | Hybrid Type | Hybrid Color | Female Parent | Female Type | Female Color | Male Parent | Male Type | Male Color |
|---|---|---|---|---|---|---|---|---|
| gfG2046 | gf | greenish rose splash | 1512A-2-1-1 | mf | red | *2171-1-3-3-1 | gf | green |
| gfG2134 | gf | antique rose | *2171-1-3-3-1 | gf | green | 2199-1-1-2 | mf | salmon |
| gfG2133 | gf | antique rose | *2171-1-3-3-1 | gf | green | 2018-2-1-1 | mf | rose |
| gfG2131 | gf | greenish pink | *2171-1-3-3-1 | gf | green | 2053A-1 | mf mf | rose morn pattern |
| gfG2045 | gf | antique lilac | 1623A-5-1 | mf | sky bluish purple | *2171-1-3-3-1 | gf | green |
| gfG2136 | gf | antique rose | 2183-3-3-1-3 | gf | red | *2171-1-1-5-2 | mf | green |
| gfG2140 | gf | green | *2171-1-1-5-2 | mf | green | 1947-1-2-2 | gf | white |

As shown in Table 1, the gc1-1 allele of the present invention can be readily transferred to a hybrid *petunia* plant from either the male or female parent plant. Also as shown in Table 1, the mutant allele results in various new and unexpected flower colors and color patterns when crossed into different *petunia* genetic backgrounds.

Example 4

Introgression of Mutant Allele gc1-1 into *Petunia* to Produce Novel Flower Color *Multiflora Petunia* Hybrids The mutant plant 2171-1 containing the mutant allele gc1-1 of the present invention was also crossed with different *petunia* genetic backgrounds. Crosses were done by controlled bud pollination. The progeny seeds were sown and grown under controlled greenhouse conditions. Desirable plants were selected and self-pollinated or re-crossed with chosen breeding lines. Many plants with novel colors were derived from these crosses either in the first generation populations or the following generation populations.

In 2005, the inbred *multiflora* line 2171-1-1-5-2 described in Example 2 above and containing the mutant allele gc1-1 of the present invention was crossed as either the male or female parent with PanAmerican seed proprietary breeding lines to create several *multiflora* hybrids having novel flower color. Some examples are listed in Table 2 below.

As shown in Table 2, column 1 shows the number assigned to each hybrid, column 2 shows the type of hybrid, *multiflora* (mf), column 3 shows the flower color of the hybrid, column 4 shows the number assigned to the female parent of the hybrid, column 5 shows the plant type of the female parent of the hybrid *multiflora* (mf) column 6 shows the flower color of the female parent of the hybrid, column 7 shows the number assigned to the male parent of the hybrid, column 8 shows the plant type of the male parent of the hybrid (mf) and column 9 shows the flower color of the male parent of the hybrid. The asterisk next to the number of the female parent or male parent of the hybrid indicates that particular parent contains the gc1-1 allele.

TABLE 2

Multiflora *Petunia* Hybrids

| Hybrid Number | Hybrid Type | Hybrid Color | Female Inbred | Female Type | Female Color | Male Inbred | Male Type | Male Color |
|---|---|---|---|---|---|---|---|---|
| mfG2139 | mf | antique pink | 2053A-1 | mf | rose morn pattern | *2171-1-1-5-2 | mf | green |
| mfG2143 | mf | green | *2171-1-1-5-2 | mf | green | 1154A-1-1 | mf | yellow |
| mfG2138 | mf | green | 1947-2-2-3-2 | mf | white | *2171-1-1-5-2 | mf | green |
| mfG2145 | mf | antique rose | 2199-1-1-2 | mf | salmon | *2171-1-1-5-2 | mf | green |
| mfG2144 | mf | antique lilac | *2171-1-1-5-2 | mf | green | 1623A-5-1 | mf | sky bluish purple |
| mfG2146 | mf | magenta-yellow | 2229-1-1-2 | mf | bluish purple morn pattern | *2171-1-1-5-2 | mf | green |
| mfG2147 | mf | magenta burgundy | 5236-1-1-1-2 | mf | bluish purple | *2171-1-1-5-2 | mf | green |

As shown in Table 2, the gc1-1 allele can be readily transferred to a hybrid *petunia* plant from either the male or female parent plant. Also as shown in Table 2, the mutant allele results in various new and unexpected flower colors and color patterns when crossed into different *petunia* genetic backgrounds.

Example 5

Introgression of Mutant Allele gc1-1 into
*Grandiflora Petunia* Breeding Lines to Produce
Novel Flower Color *Petunia* Breeding Family 1

The mutant plant 2171-1 containing the mutant allele gc1-1 of the present invention or a selected plant from progeny of 2171-1 containing the mutant allele gc1-1 of the present invention was crossed with different *grandiflora petunia* genetic backgrounds to create a population of *petunia* breeding families. Crosses were done by controlled bud pollination. The progeny seeds were sown and grown under controlled greenhouse conditions. Desirable plants were selected and self-pollinated or crossed again with chosen breeding lines. Plants having a wide range of novel colors and shades of these colors were derived from these crosses either in the first generation population or the following generation populations.

One cross was between the mutant 2171-1 containing the mutant allele gc1-1 of the present invention and the Pan-American seed proprietary breeding line 2090-2-2 having yellow *grandiflora* flowers. The resultant $F_1$ population designated as breeding family 2240 and containing the mutant allele gc1-1 of the present invention segregated for *grandiflora* and *multiflora* type flowers having flower colors of green, white, and unexpectedly, a pink with yellow star pattern. In the $F_2$ or later generations, flower sizes segregated into large and small and flower colors of green and white.

Example 6

Introgression of Mutant Allele gc1-1 into
*Grandiflora Petunia* Breeding Lines to Produce
Novel Flower Color *Petunia* Breeding Family 2

The mutant plant 2171-1 containing the mutant allele gc1-1 of the present invention or a selected plant from progeny of 2171-1 containing the mutant allele gc1-1 of the present invention was crossed with different *grandiflora petunia* genetic backgrounds to create a population of *petunia* breeding families. Crosses were done by controlled bud pollination. The progeny seeds were sown and grown under controlled greenhouse conditions. Desirable plants were selected and self-pollinated or crossed again with chosen breeding lines. Plants having a wide range of novel colors and shades of these colors were derived from these crosses either in the first generation population or the following generation populations.

Another cross was between 2171-1-1, a mutant-derived plant having green *grandiflora* flowers and containing the mutant allele gc1-1 of the present invention, and the Pan-American seed proprietary breeding line 2233-3 having creamy yellow *grandiflora* flowers. The resultant $F_1$ population designated as breeding family 2258 and containing the mutant allele gc1-1 of the present invention segregated for *grandiflora* and *multiflora* type flowers having flower colors of green, yellow and greenish pink. In the $F_2$ or later generations, flower colors included antique pink, antique burgundy, antique terracotta, orange, yellow, and terracotta morn pattern.

Example 7

Introgression of Mutant Allele gc1-1 into
*Grandiflora Petunia* Breeding Lines to Produce
Novel Flower Color *Petunia* Breeding Family 3

The mutant plant 2171-1 containing the mutant allele gc1-1 of the present invention or a selected plant from progeny of 2171-1 containing the mutant allele gc1-1 of the present invention was crossed with different *grandiflora petunia* genetic backgrounds to create a population of *petunia* breeding families. Crosses were done by controlled bud pollination. The progeny seeds were sown and grown under controlled greenhouse conditions. Desirable plants were selected and self-pollinated or crossed again with chosen breeding lines. Plants having a wide range of novel colors and shades of these colors were derived from these crosses either in the first generation population or the following generation populations.

Another cross was between 2171-1-3, a mutant-derived plant having green *grandiflora* flowers and containing the mutant allele gc1-1 of the present invention, and the Pan-American seed proprietary breeding line 2234-2 having creamy yellow *grandiflora* flowers. The resultant $F_1$ population designated as breeding family 2259 and containing the mutant allele gc1-1 of the present invention segregated for *grandiflora* and *multiflora* type flowers having flower colors of white, green, creamy yellow and terracotta. In the $F_2$ or later generations, flower colors included green, white, antique rose, peach, and orange-peach.

Example 8

Introgression of Mutant Allele gc1-1 into
*Grandiflora Petunia* Breeding Lines to Produce
Novel Flower Color *Petunia* Breeding Family 4

The mutant plant 2171-1 containing the mutant allele gc1-1 of the present invention or a selected plant from progeny of 2171-1 containing the mutant allele gc1-1 of the present invention was crossed with different *grandiflora petunia* genetic backgrounds to create a population of *petunia* breeding families. Crosses were done by controlled bud pollination. The progeny seeds were sown and grown under controlled greenhouse conditions. Desirable plants were selected and self-pollinated or crossed again with chosen breeding lines. Plants having a wide range of novel colors and shades of these colors were derived from these crosses either in the first generation population or the following generation populations.

The mutant 2171-1 containing the mutant allele gc1-1 of the present invention was used as the female parent in a cross with the male parent PanAmerican seed proprietary breeding line 2086-1-1 having greenish-white *multiflora* flowers. One $F_4$ plant from this cross having burgundy with yellow star pattern *multiflora* flowers was identified as 2239-1-1-4-6. Plant 2239-1-1-4-6 containing the mutant allele gc1-1 of the present invention was used as the female parent in a cross with the male parent Pan American seed proprietary breeding line 2323-1 having red with a white star pattern *grandiflora* flowers. The resultant $F_1$ population designated as breeding family 2446 and containing the mutant allele gc1-1 of the present invention segregated for *grandiflora* and *multiflora* type flowers having flower colors of yellow, burgundy with a yellow star pattern, and red with a yellow star pattern.

Example 9

Introgression of Mutant Allele gc1-1 into *Grandiflora Petunia* Breeding Lines to Produce Novel Flower Color *Petunia* Breeding Family 5

The mutant plant 2171-1 containing the mutant allele gc1-1 of the present invention or a selected plant from progeny of 2171-1 containing the mutant allele gc1-1 of the present invention was crossed with different *grandiflora petunia* genetic backgrounds to create a population of *petunia* breeding families. Crosses were done by controlled bud pollination. The progeny seeds were sown and grown under controlled greenhouse conditions. Desirable plants were selected and self-pollinated or crossed again with chosen breeding lines. Plants having a wide range of novel colors and shades of these colors were derived from these crosses either in the first generation population or the following generation populations.

The mutant 2171-1 containing the mutant allele gc1-1 of the present invention was used as the female parent in a cross with the male parent PanAmerican seed proprietary breeding line 2086-1-1 having greenish-white *multiflora* flowers. One $F_4$ selection having burgundy with a yellow star pattern *multiflora* flowers was identified as 2239-1-1-4-4. Plant 2239-1-1-4-4 containing the mutant allele gc1-1 of the present invention was used as the female parent in a cross with the male parent PanAmerican seed proprietary breeding line 2328-7 having bluish-purple with a white star pattern *grandiflora* flowers. The resultant $F_1$ population designated as breeding family 2445 and containing the mutant allele gc1-1 of the present invention segregated for *grandiflora* and *multiflora* type flowers having flower colors of yellow and bluish-burgundy with a yellow star pattern.

Example 10

Introgression of Mutant Allele gc1-1 into *Multiflora Petunia* Breeding Lines to Produce Novel Flower Color *Petunia* Breeding Family 1

The mutant plant 2171-1 containing the mutant allele gc1-1 of the present invention or a selected plant from progeny of 2171-1 containing the mutant allele gc1-1 of the present invention was crossed with different *multiflora petunia* genetic backgrounds to create a population of *petunia* breeding families. Crosses were done by controlled bud pollination. The progeny seeds were sown and grown under controlled greenhouse conditions. Desirable plants were selected and self-pollinated or crossed again with chosen breeding lines. Plants having a wide range of novel colors and shades of these colors were derived from these crosses either in the first generation population or the following generation populations.

One cross was between the mutant 2171-1 containing the mutant allele gc1-1 of the present invention and the PanAmerican seed proprietary breeding line 2086-1-1 having greenish-white *multiflora* flowers. The resultant $F_1$ population designated as breeding family 2239 and containing the mutant allele gc1-1 of the present invention segregated for *grandiflora* and *multiflora* type flowers having flower colors of green, white, and greenish-blush pink. In the $F_2$ or later generations, flower colors included green, white, and unexpectedly pink-blush, creamy yellow, terracotta, and burgundy with a yellow star pattern.

Example 11

Introgression of Mutant Allele gc1-1 into *Multiflora Petunia* Breeding Lines to Produce Novel Flower Color *Petunia* Breeding Family 2

The mutant plant 2171-1 containing the mutant allele gc1-1 of the present invention or a selected plant from progeny of 2171-1 containing the mutant allele gc1-1 of the present invention was crossed with different *multiflora petunia* genetic backgrounds to create a population of *petunia* breeding families. Crosses were done by controlled bud pollination. The progeny seeds were sown and grown under controlled greenhouse conditions. Desirable plants were selected and self-pollinated or crossed again with chosen breeding lines. Plants having a wide range of novel colors and shades of these colors were derived from these crosses either in the first generation population or the following generation populations.

Another cross was between the mutant 2171-1 containing the mutant allele gc1-1 of the present invention and the PanAmerican seed proprietary breeding line 5199-4 having yellow *multiflora* flowers. The resultant $F_1$ population designated as breeding family 2241 and containing the mutant allele gc1-1 of the present invention segregated for *grandiflora* and *multiflora* type flowers having flower colors of green and white. In the $F_2$ or later generations, flower colors included green, white, terracotta, greenish-pink, and creamy yellow.

Example 12

Introgression of Mutant Allele gc1-1 into *Multiflora Petunia* Breeding Lines to Produce Novel Color *Petunia* Breeding Family 3

The mutant plant 2171-1 containing the mutant allele gc1-1 of the present invention or a selected plant from progeny of 2171-1 containing the mutant allele gc1-1 of the present invention was crossed with different *multiflora petunia* genetic backgrounds to create a population of *petunia* breeding families. Crosses were done by controlled bud pollination. The progeny seeds were sown and grown under controlled greenhouse conditions. Desirable plants were selected and self-pollinated or crossed again with chosen breeding lines. Plants having a wide range of novel colors and shades of these colors were derived from these crosses either in the first generation population or the following generation populations.

Another cross was between 2171 B-5, a mutant-derived plant having green *grandiflora* flowers and containing the mutant allele gc1-1 of the present invention, and the PanAmerican seed proprietary breeding line 1512A-2-1-1 having red *multiflora* flowers. The resultant $F_1$ population designated as breeding family 2046 and containing the mutant allele gc1-1 of the present invention and having flower colors of rose with a greenish-yellow blush or a partial star pattern. Unexpectedly the $F_2$ population segregated for *grandiflora* and *multiflora* type flowers having flower colors of green, rose, peach, pink blush, antique rose, rose blush, and rose with yellow in a partial star pattern.

Example 13

**Introgression of Mutant Allele gc1-1 into *Multiflora Petunia* Breeding Lines to Produce Novel Flower Color *Petunia* Breeding Family 4**

The mutant plant 2171-1 containing the mutant allele gc1-1 of the present invention or a selected plant from progeny of 2171-1 containing the mutant allele gc1-1 of the present invention was crossed with different *multiflora petunia* genetic backgrounds to create a population of *petunia* breeding families. Crosses were done by controlled bud pollination. The progeny seeds were sown and grown under controlled greenhouse conditions. Desirable plants were selected and self-pollinated or crossed again with chosen breeding lines. Plants having a wide range of novel colors and shades of these colors were derived from these crosses either in the first generation population or the following generation populations.

Another cross was between 2171A-2-3, a mutant-derived plant having green *multiflora* flowers and containing the mutant allele gc1-1 of the present invention, and the PanAmerican seed proprietary breeding line 5236-1-1-1-2 having bluish-purple *multiflora* flowers. The resultant $F_1$ population designated as breeding family 2147 and containing the mutant allele gc1-1 of the present invention segregated for flower colors of magenta and burgundy.

Example 14

**Introgression of Mutant Allele gc1-1 into *Multiflora Petunia* Breeding Lines to Produce Novel Flower Color *Petunia* Breeding Family 5**

The mutant plant 2171-1 containing the mutant allele gc1-1 of the present invention or a selected plant from progeny of 2171-1 containing the mutant allele gc1-1 of the present invention was crossed with different *multiflora petunia* genetic backgrounds to create a population of *petunia* breeding families. Crosses were done by controlled bud pollination. The progeny seeds were sown and grown under controlled greenhouse conditions. Desirable plants were selected and self-pollinated or crossed again with chosen breeding lines. Plants having a wide range of novel colors and shades of these colors were derived from these crosses either in the first generation population or the following generation populations.

Another cross was between 2171B-5-2, a mutant-derived plant having green *grandiflora* flowers and containing the mutant allele gc1-1 of the present invention, and the PanAmerican seed proprietary breeding line 2018-2-1-1 having rose *multiflora* flowers. The resultant $F_1$ population designated as breeding family 2133 and containing the mutant allele gc1-1 of the present invention segregated for *grandiflora* and *multiflora* type flowers having an antique rose flower color.

Example 15

**Introgression of Mutant Allele gc1-1 into *Multiflora Petunia* Breeding Lines to Produce Novel Flower Color *Petunia* Breeding Family 6**

The mutant plant 2171-1 containing the mutant allele gc1-1 of the present invention or a selected plant from progeny of 2171-1 containing the mutant allele gc1-1 of the present invention was crossed with different *multiflora petunia* genetic backgrounds to create a population of *petunia* breeding families. Crosses were done by controlled bud pollination. The progeny seeds were sown and grown under controlled greenhouse conditions. Desirable plants were selected and self-pollinated or crossed again with chosen breeding lines. Plants having a wide range of novel colors and shades of these colors were derived from these crosses either in the first generation population or the following generation populations.

Another cross was between 2171A-2-4, a mutant-derived plant having green *multiflora* flowers and containing the mutant allele gc1-1 of the present invention, and the PanAmerican seed proprietary breeding line 2053A-1 having rose morn pattern *multiflora* flowers. The resultant $F_1$ population designated as breeding family 2139 and containing the mutant allele gc1-1 of the present invention with flower colors of greenish-pink. The $F_2$ population segregated for flower colors of antique pink morn, antique rose morn, green, and white.

Example 16

**Introgression of Mutant Allele gc1-1 into Large and Small-Sized *Multiflora* Flower Spreading-Type *Petunia* Breeding Lines to Produce Novel Flower Color *Petunia* Breeding Family 1**

The mutant plant 2171-1 containing the mutant allele gc1-1 of the present invention or a selected plant from progeny of 2171-1 containing the mutant allele gc1-1 of the present invention was crossed with different *multiflora spreading petunia* genetic backgrounds to create a population of spreading *petunia* breeding families. Crosses were done by controlled bud pollination. The progeny seeds were sown and grown under controlled greenhouse conditions. Desirable plants were selected and self-pollinated or crossed again with chosen breeding lines. Plants having a wide range of novel colors and shades of these colors were derived from these crosses either in the first generation population or the following generation populations.

One cross was between 2171-1-3, a mutant-derived plant having green *grandiflora* flowers and containing the mutant allele gc1-1 of the present invention, and the PanAmerican seed proprietary breeding line 5239-1-4 having small-sized flowers with a green picotee, purple veined flower color and a spreading-type growth habit. The resultant $F_1$ population designated as breeding family 2289 and containing the mutant allele gc1-1 of the present invention segregated for *grandiflora* and *multiflora* type flowers having flower colors of magenta, greenish-pink, purple, and white.

Example 17

**Introgression of Mutant Allele gc1-1 into Large and Small-Sized *Multiflora* Flower Spreading-Type *Petunia* Breeding Lines to Produce Novel Flower Color *Petunia* Breeding Family 2**

The mutant plant 2171-1 containing the mutant allele gc1-1 of the present invention or a selected plant from progeny of 2171-1 containing the mutant allele gc1-1 of the present invention was crossed with different *multiflora spreading petunia* genetic backgrounds to create a population of spreading *petunia* breeding families. Crosses were done by controlled bud pollination. The progeny seeds were sown and grown under controlled greenhouse conditions. Desirable plants were selected and self-pollinated or crossed again with chosen breeding lines. Plants having a wide range of novel colors and shades of these colors were derived from these crosses either in the first generation population or the following generation populations.

The mutant 2171-1 containing the mutant allele gc1-1 of the present invention was used as the female parent in a cross with the male parent PanAmerican seed proprietary breeding line 5199-4 having yellow *multiflora* flowers and a spreading habit. One selection having green *multiflora* flowers in the created family designated as breeding family 2241 was identified as 2241-2. Plant 2241-2 containing the mutant allele gc1-1 of the present invention was used as the female parent in a cross with the male parent PanAmerican seed proprietary breeding line 5238-2-9 having small-sized, white-colored flowers, and a spreading-type growth habit. The resultant $F_1$ population designated as breeding family 5404 and containing the mutant allele gc1-1 of the present invention segregated as small flower and large flower size having flower colors of cream, green, and terracotta. In the $F_2$ or later generations, flower colors included green, white, terracotta, cream, and antique rose.

Example 18

Introgression of Mutant Allele gc1-1 into Large and Small-Sized *Multiflora* Flower Spreading-Type *Petunia* Breeding Lines to Produce Novel Flower Color *Petunia* Breeding Family 3

The mutant plant 2171-1 containing the mutant allele gc1-1 of the present invention or a selected plant from progeny of 2171-1 containing the mutant allele gc1-1 of the present invention was crossed with different *multiflora* spreading *petunia* genetic backgrounds to create a population of spreading *petunia* breeding families. Crosses were done by controlled bud pollination. The progeny seeds were sown and grown under controlled greenhouse conditions. Desirable plants were selected and self-pollinated or crossed again with chosen breeding lines. Plants having a wide range of novel colors and shades of these colors were derived from these crosses either in the first generation population or the following generation populations.

From the above identified 5404 breeding family containing the mutant allele gc1-1 of the present invention, one selection having small-sized, greenish-pink-colored flowers and spreading growth habit was identified as 5404-5. Plant 5404-5 containing the mutant allele gc1-1 of the present invention was used as the female parent with the male parent PanAmerican seed proprietary breeding line 5429-4 having small-sized, silver-white colored flowers, and a spreading-type growth habit. The resultant $F_1$ population designated as breeding family 5458 and containing the mutant allele gc1-1 of the present invention had small-sized flowers and segregated for plant vigor, growth habit, flower color and color pattern. Among others, the flower colors include burgundy, coral rose, bluish-purple, antique coral, antique green, and, unexpectedly black, and black-green blush. In addition, unexpected veined-patterned plants were observed.

Example 19

Introgression of Mutant Allele gc1-1 into Large and Small-Sized *Multiflora* Flower Spreading-Type *Petunia* Breeding Lines to Produce Novel Flower Color *Petunia* Breeding Family 4

The mutant plant 2171-1 containing the mutant allele gc1-1 of the present invention or a selected plant from progeny of 2171-1 containing the mutant allele gc1-1 of the present invention was crossed with different *multiflora* spreading *petunia* genetic backgrounds to create a population of spreading *petunia* breeding families. Crosses were done by controlled bud pollination. The progeny seeds were sown and grown under controlled greenhouse conditions. Desirable plants were selected and self-pollinated or crossed again with chosen breeding lines. Plants having a wide range of novel colors and shades of these colors were derived from these crosses either in the first generation population or the following generation populations.

From the above identified 5458 breeding family containing the mutant allele gc1-1 of the present invention, one selection having small-sized, greenish-pink-colored flowers and a spreading growth habit was identified as 5458D-3. Plant 5458D-3 containing the mutant allele gc1-1 of the present invention was used as the female parent with the male parent PanAmerican seed proprietary breeding line 4621-1-1-1 having large-sized, light bluish-purple-colored flowers, and a spreading-type growth habit. The resultant $F_1$ population designated as breeding family 4884 and containing the mutant allele gc1-1 of the present invention had smaller-sized flowers having flower colors of peach, lilac, purple, and shades of salmon.

Example 20

Introgression of Mutant Allele gc1-1 into Large and Small-Sized *Multiflora* Flower Spreading-Type *Petunia* Breeding Lines to Produce Novel Flower Color *Petunia* Breeding Family 5

The mutant plant 2171-1 containing the mutant allele gc1-1 of the present invention or a selected plant from progeny of 2171-1 containing the mutant allele gc1-1 of the present invention was crossed with different *multiflora* spreading *petunia* genetic backgrounds to create a population of spreading *petunia* breeding families. Crosses were done by controlled bud pollination. The progeny seeds were sown and grown under controlled greenhouse conditions. Desirable plants were selected and self-pollinated or crossed again with chosen breeding lines. Plants having a wide range of novel colors and shades of these colors were derived from these crosses either in the first generation population or the following generation populations.

From the above identified 5458 breeding family, one selection having small-sized bluish-purple-colored flowers and a spreading growing habit was identified as 5458C-3. Plant 5458C-3 containing the mutant allele gc1-1 of the present invention was used as the female parent with the male parent PanAmerican seed proprietary breeding line 4626-2-3-2 having large-sized, bluish-purple-colored flowers and a spreading-type growth habit. The resultant $F_1$ population designated as breeding family 4886 and contained the mutant allele gc1-1 of the present invention had smaller-sized flowers having flower colors of lavender, deep purple velvet, and burgundy.

Example 21

Introgression of Mutant Allele gc1-1 into Large- and Small-Sized *Multiflora* Flower Spreading-Type *Petunia* Breeding Lines to Produce Novel Flower Color *Petunia* Breeding Family 6

The mutant plant 2171-1 containing the mutant allele gc1-1 of the present invention or a selected plant from progeny of 2171-1 containing the mutant allele gc1-1 of the present invention was crossed with different *multiflora* spreading *petunia* genetic backgrounds to create a population of spreading *petunia* breeding families. Crosses were done by controlled bud pollination. The progeny seeds were sown and grown under controlled greenhouse conditions. Desirable plants were selected and self-pollinated or crossed again with chosen breeding lines. Plants having a wide range of novel colors and shades of these colors were derived from these crosses either in the first generation population or the following generation populations.

From the previously described 2445 breeding family, one selection, a *grandiflora* plant having flower color of deep purple with yellow star pattern was identified as 2445-1. Plant 2445-1 containing the mutant allele gc1-1 of the present invention was used as the female parent with the male parent PanAmerican seed proprietary breeding line 4624-2-4-1 having large-sized, bluish-purple-colored flowers, and a spreading-type growth habit. The resultant $F_1$ population designated as breeding family 4904 and contained the mutant allele gc1-1 of the present invention had large-sized flowers having flower colors of green, bluish purple with a yellow star pattern, and unexpectedly, dark purple velvet similar to black with a yellow star pattern.

Example 22

Introgression of Mutant Allele gc1-1 into Double-Flowered *Petunia* Breeding Lines to Produce Novel Flower Color Double *Petunia* Breeding Families The mutant plant 2171-1 containing the mutant allele gc1-1 of the present invention was crossed with different double-flowered *petunia* genetic backgrounds to create a population of double *petunia* breeding families. Desirable plants are selected and self-pollinated or crossed again with chosen breeding lines. Many plants with novel colors are derived from these crosses either in the first generation populations or the following generation populations.

Example 23

Introgression of Mutant Allele gc1-1 into Veined-Type *Petunia* Breeding Lines to Produce Novel Flower Color *Petunia* Breeding Families The mutant plant 2171-1 containing the mutant allele gc1-1 of the present invention is crossed with different veined-type *petunia* genetic backgrounds to create a population of novel color *petunia* breeding families. Desirable plants are selected and self-pollinated or crossed again with chosen breeding lines. Many plants with novel colors are derived from these crosses either in the first generation populations or the following generation populations.

Example 24

Introgression of Mutant Allele gc1-1 into Picotee-Type *Petunia* Breeding Lines to Produce Novel Flower Color *Petunia* Breeding Families The mutant plant 2171-1 containing the mutant allele gc1-1 of the present invention was crossed with different picotee-type *petunia* genetic backgrounds to create a population of novel pictoee *petunia* breeding families. Desirable plants are selected and self-pollinated or crossed again with chosen breeding lines. Many plants with novel colors are derived from these crosses either in the first generation populations or the following generation populations.

Example 25

Introgression of Mutant Allele gc1-1 into *Calibrachoa-Petunia* Breeding Lines to Produce Novel Flower Color *Calibrachoa-Petunia* Breeding Families The mutant plant 2171-1 containing the mutant allele gc1-1 of the present invention is crossed with different *Calibrachoa* genetic backgrounds to create a population of *calibrachoa-petunia* breeding families. The *calibrachoa-petunia* breeding family having unique flower color as the result of mutant allele gc1-1 being introgressed is developed using an intergeneric cross between the mutant *petunia* plant 2171-1 containing the mutant allele gc1-1 of the present invention and a *calibrachoa* plant. After crossing the parent lines, the ovules are removed from flowers on the female parent and cultured by standard ovule culture techniques (see for example Honda et al. (2003) *Euphytica* 129(3):275-279; Reed, S. and G. B. Collins (1978) *J. Hered.* 69(5):311-315; Chi, H. S. (2002) *Bot. Bull. Acad. Sin.* 43:139-146. The resulting intergeneric hybrid plantlets are then transplanted for greenhouse culture and acclimatization.

Example 26

Transformation of Mutant Allele gc1-1 into *Calibrachoa* to Produce Novel Flower Color *Calibrachoa* Plants A *Calibrachoa* plant, or a part thereof, is transformed with the mutant allele gc1-1 to produce a *Calibrachoa* plant with a unique flower color and/or color pattern using standard transformation techniques and standard regeneration techniques.

Example 27

Transformation of Mutant Allele gc1-1 cDNA into *Petunia* or *Calibrachoa* to Produce Novel Flower Color *Petunia* or *Calibrachoa* Plants A *Petunia* plant, or a part thereof, is transformed with a cDNA of the mutant allele gc1-1 to produce a *Petunia* plant with a unique flower color and/or color pattern using standard transformation techniques and standard regeneration techniques. Likewise, a *Calibrachoa* plant, or a part thereof, is transformed with a cDNA of the mutant allele gc1-1 to produce a *Calibrachoa* plant with a unique flower color and/or color pattern using standard transformation techniques and standard regeneration techniques.

Example 28

The Effect of Mutant Allele gc1-1 on Plastid Development in *Petunia* Flower Corollas Plastids can undergo several differentiation pathways, the nature of which is dependent on the cell type in which the plastid resides. The most well-known developmental pathway is the proplastid-to-chloroplast transition during the development of leaves. Another well-studied example is the chloroplast-to-chromoplast transition that occurs during tomato fruit ripening or marigold flower development in which the chromoplast accumulates carotenoids for color display. While the former example demonstrates a differentiation pathway that can arise directly from proplastids (undifferentiated plastids) in meristem cells, the latter example demonstrates that interconversion and redifferentiation of different plastid types can also occur. A study was conducted to determine if mutant allele gc1-1 had any effect on plastid differentiation in *petunia* corollas. For this study, an ultrastructural analysis of the plastid type and structure in the corollas wild-type and gc1-1 *petunias* was undertaken.

The plastids in wild-type white-flowering *petunia* corollas are colorless and have been termed leucoplasts after the terminology of Kirk and Tilney-Bassett (1978). In electron micrographs, these leucoplasts are characterized by a lack of internal plastid structures, with few, if any, thylakoid membranes or thylakoid stacks. They also appeared to be reduced in size compared to the plastid types subsequently analyzed in gc1-1 corollas.

In sharp contrast to the generic nature of the leucoplasts found in wild-type white *petunia* corollas, the plastid structures in the gc1-1-containing green corollas of plant 2171 displayed numerous ultrastructural features. First, they displayed prominent thylakoid membrane development distributed throughout the entire structure, reminiscent of chloroplasts. The presence of grana, or stacked thylakoid membranes, served to reinforce this notion. Second, a small number of round, densely-staining, carotenoid-containing granules was noted in this line. Finally, the size of the plastids was significantly larger than the leucoplasts found in the corolla of the white-flowering line. Taken together these observations indicated that the gc1-1 allele promoted the differentiation and maintenance of chloroplasts organelles, thus providing a structural explanation for the green color outcome associated with this mutation.

Next, a deep yellow-flowering line containing the mutant allele gc1-1, designated 2258 was examined. Ultrastructural analysis of line 2258's corolla plastids revealed the continued presence of thylakoid membranes distributed throughout their entirety. Moreover, the persistence of grana in these plastid types remained. However, the most striking feature was the size and number of carotenoid-containing granules that were observed in these plastids. Compared to the green-flowered line, 2171, these granules were significantly larger ($2\times$-$3\times$) and more numerous. Based upon this evidence, it was concluded that the yellow color outcome was based upon the accumulation of carotenoids in this gc1-1-containing line, a very different color outcome compared to 2171. HPLC analysis of pigments extracted from the deep yellow corollas confirmed their identity as carotenoids, primarily beta-carotene and lutein. This result indicated that the phenotype of the lines carrying the gc1-1 allele was subject to modification by other genes/alleles in the *petunia* genome.

In the normal chloroplast-to-chromoplast transition in other plant tissues (e.g., tomato fruit), the thylakoid membranes and grana deteriorate and become a much less-structured membrane system. In fully differentiated chromoplasts, carotenoid-containing structures (e.g., plastoglobules) become the predominant structural feature. However, the plastids in 2258 simultaneously displayed both chloroplast-associated features (extensive thylakoid membranes and grana) and chromoplast-associated features (accumulation of carotenoid-containing granules). The coexistence of high levels of thylakoid grana and the carotenoid-containing granules in the plastid suggest that the normal developmental transition between chloroplast and chromoplast has been disrupted.

The $F_1$ hybrid 'Summer Sun' is an older *petunia* variety that lacks the gc1-1 mutant allele but exhibits yellow flowers overall, with the intervascular region being a creamy to light-yellow color and the vascular region displaying a more intense pigmentation. The plastid structure in the intervascular region of the corolla was typified by few, if any, thylakoid membranes and only remnants of thylakoid stacks. The most prominent feature was the abundance and size of the circular, carotenoid-containing granules located throughout the internal expanse of the plastid. The noticeable lack of chloroplast-associated features and prominent carotenoid-associated features identified these plastids as having followed the differentiation pathway to chromoplasts. 'Summer Sun' petal plastids were not characterized by the coexistence of chloroplast- and chromoplast-associated ultrastructural elements as is seen in the petals of 2258 plants containing the gc1-1 mutant allele.

Example 29

Transformation of Mutant Allele gc1-1 cDNA into Ornamental Plants to Produce Novel Flower Color Ornamental Plants An ornamental plant, or a part thereof, is transformed with a cDNA of the mutant allele gc1-1 to produce an ornamental plant with a unique flower color and/or color pattern using standard transformation techniques and standard regeneration techniques.

Example 30

Production of an Ornamental Plant with Altered Flower Color and/or Altered Flower Color Pattern An ornamental plant with altered flower color and/or altered flower color pattern is produced by crossing a *petunia* plant containing the mutant allele gc1-1 with an ornamental plant, harvesting the hybrid embryo produced by the cross using standard embryo rescue techniques, and regenerating a hybrid plant using standard regeneration techniques. An ornamental plant with altered flower color and/or altered flower color pattern is produced by crossing a *petunia* plant containing the mutant allele gc1-1 with an ornamental plant, harvesting the seed produced by the cross, and planting and growing the seed thereby producing an ornamental plant with altered flower color and/or altered flower color pattern.

Further Embodiments of the Invention

This invention also is directed to methods for producing a *petunia* plant by crossing a first parent *petunia* plant with a second parent *petunia* plant wherein either the first or second parent *petunia* plant contains the gc1-1 allele of the present invention. Further, this invention also is directed to methods for producing an inbred *petunia* line gc1-1-derived *petunia* plant by crossing an inbred *petunia* line containing the gc1-1 allele with a second *petunia* plant and growing the progeny seed, and repeating the crossing and growing steps with the inbred *petunia* line gc1-1-derived plant from 1, 2, 3, 4, 5, 6 to 7 times. Thus, any such methods using a *petunia* line containing the gc1-1 allele are part of this invention: selfing, backcrosses, hybrid production, crosses to populations, and the like. All plants produced using a *petunia* line containing the gc1-1 allele as a parent are within the scope of this invention, including plants derived from inbred *petunia* lines having gc1-1.

As used herein, the term plant includes plant cells, plant protoplasts, plant cell tissue cultures from which *petunia* plants can be regenerated, plant calli, plant clumps and plant cells that are intact in plants or parts of plants, such as embryos, pollen, ovules, flowers, pistils, anthers, leaves, stems, and the like.

As it is well known in the art, tissue culture of *petunia* can be used for the in vitro regeneration of *petunia* plants. Tissues cultures of various tissues of *petunia* and regeneration of plants therefrom are well known and published. By way of example, a tissue culture comprising organs has been used to produce regenerated plants as described in Regeneration and Micropropagation: Techniques, Systems and Media 1991-1995, in Herman, E. B., ed., *Recent Advances in Plant Tissue Culture*, Volume 3 (1995); Desamero et al., *Plant Cell Tiss. Org. Cult.* 33:265-271 (1993); Tabei et al., *Plant Tiss. Cult. Lett.* 10:235 (1993). Thus, another aspect of this invention is to provide cells which, upon growth and differentiation, produce *petunia* plants having the physiological and morphological characteristics of a *petunia* line containing the gc1-1 allele.

With the advent of molecular biological techniques allowing the isolation and characterization of genes that encode specific protein products, scientists in the field of plant biology developed a strong interest in engineering the genome of plants to contain and express foreign genes, or additional or modified versions of native, or endogenous, genes (perhaps driven by different promoters) in order to alter the traits of a plant in a specific manner. Such foreign additional and/or modified genes are referred to herein collectively as "transgenes". Over the last fifteen to twenty years several methods for producing transgenic plants have been developed, and the present invention in particular embodiments also relates to transformed versions of the claimed plants having the mutant allele.

Plant transformation involves the construction of an expression vector which will function in plant cells. Such a vector comprises DNA comprising a gene under control of, or operatively linked to, a regulatory element (for example, a promoter). The expression vector may contain one or more such operably linked gene/regulatory element combinations. The vector(s) may be in the form of a plasmid, and can be used alone or in combination with other plasmids, to provide transformed *petunia* plants, using transformation methods as described below to incorporate transgenes into the genetic material of the *petunia* plant(s).

Expression Vectors for *Petunia* Transformation—Marker Genes

Expression vectors include at least one genetic marker, operably linked to a regulatory element (a promoter, for example) that allows transformed cells containing the marker to be either recovered by negative selection, i.e., inhibiting growth of cells that do not contain the selectable marker gene, or by positive selection, i.e., screening for the product encoded by the genetic marker. Many commonly used selectable marker genes for plant transformation are well known in the transformation arts, and include, for example, genes that code for enzymes that metabolically detoxify a selective chemical agent which may be an antibiotic or an herbicide, or genes that encode an altered target which is insensitive to the inhibitor. A few positive selection methods are also known in the art.

One commonly used selectable marker gene for plant transformation is the neomycin phosphotransferase II (nptII) gene, isolated from transposon Tn5, which, when placed under the control of plant regulatory signals, confers resistance to kanamycin. Fraley et al., *Proc. Natl. Acad. Sci. U.S.A.*, 80:4803 (1983) Eck et al., *Plant Cell Report*, 14:5 299-304 (1995). Another commonly used selectable marker gene is the hygromycin phosphotransferase gene which confers resistance to the antibiotic hygromycin. Vanden Elzen et al., *Plant Mol. Biol.*, 5:299 (1985).

Additional selectable marker genes of bacterial origin that confer resistance to antibiotics include gentamycin acetyl transferase, streptomycin phosphotransferase and aminoglycoside-3'-adenyl transferase, the bleomycin resistance determinant. Hayford et al., *Plant Physiol*. 86:1216 (1988), Jones et al., *Mol. Gen. Genet,* 210:86 (1987), Svab et al., *Plant Mol. Biol.* 14:197 (1990), Hille et al., *Plant Mol. Biol.* 7:171 (1986). Other selectable marker genes confer resistance to herbicides such as glyphosate, glufosinate or bromoxynil. Comai et al., *Nature* 317:741-744 (1985), Gordon-Kamm et al., *Plant Cell* 2:603-618 (1990) and Stalker et al., *Science* 242:419-423 (1988).

Selectable marker genes for plant transformation which are not of bacterial origin include, for example, mouse dihydrofolate reductase, plant 5-enol-pyruvyl-shikimate-3-phosphate synthase and plant acetolactate synthase. Eichholtz et al., *Somatic Cell Mol. Genet* 13:67 (1987), Shah et al., *Science* 233:478 (1986), Charest et al., *Plant Cell Rep.* 8:643 (1990).

Another class of marker genes for plant transformation requires screening of presumptively transformed plant cells rather than direct genetic selection of transformed cells for resistance to a toxic substance such as an antibiotic. These genes are particularly useful to quantify or visualize the spatial pattern of expression of a gene in specific tissues and are frequently referred to as reporter genes because they can be fused to a gene or gene regulatory sequence for the investigation of gene expression. Commonly used genes for screening presumptively transformed cells include beta-glucuronidase (GUS), alpha-galactosidase, luciferase and chloramphenicol acetyltransferase. Jefferson, R. A., *Plant Mol. Biol. Rep.* 5:387 (1987), Teeri et al., *EMBO J.* 8:343 (1989), Koncz et al., *Proc. Natl. Acad. Sci U.S.A.* 84:131 (1987), DeBlock et al., *EMBO J.* 3:1681 (1984), Charng et al., *Plant Science Limerick.* 1994, 98: 2, 175-183, Hu Wei e al., *In vitro Cellular and Developmental Biology Plant* 37:1 12-18 (2001), Agharbaoui et al., *Plant Cell Report* 15:1/2 102-105 (1995).

In vivo methods for visualizing GUS activity that do not require destruction of plant tissue are available. Molecular Probes publication 2908, Imagene Green™, p. 1-4 (1993) and Naleway et al., *J. Cell Biol.* 115:151a (1991). However, these in vivo methods for visualizing GUS activity have not proven useful for recovery of transformed cells because of low sensitivity, high fluorescent backgrounds and limitations associated with the use of luciferase genes as selectable markers.

A gene encoding Green Fluorescent Protein (GFP) has been utilized as a marker for gene expression in prokaryotic and eukaryotic cells. Chalfie et al., *Science* 263:802 (1994). GFP and mutants of GFP may be used as screenable markers.

Expression Vectors for *Petunia* Transformation—Promoters

Genes included in expression vectors must be driven by a nucleotide sequence comprising a regulatory element, for example, a promoter. Several types of promoters are now well known in the transformation arts, as are other regulatory elements that can be used alone or in combination with promoters.

As used herein, "promoter" includes reference to a region of DNA upstream from the start of transcription and involved in recognition and binding of RNA polymerase and other proteins to initiate transcription. A plant promoter is a promoter capable of initiating transcription in plant cells.

Examples of promoters under developmental control include promoters that preferentially initiate transcription in certain tissues, such as leaves, roots, seeds, fibers, xylem vessels, tracheids, or sclerenchyma. Such promoters are referred to as "tissue-preferred". Promoters which initiate transcription only in certain tissue are referred to as "tissue-specific". A "cell type" specific promoter primarily drives expression in certain cell types in one or more organs, for example, vascular cells in roots or leaves. An "inducible" promoter is a promoter which is under environmental control. Examples of environmental conditions that may effect transcription by inducible promoters include anaerobic conditions or the presence of light. Tissue-specific, tissue-preferred, cell type specific, and inducible promoters constitute the class of "non-constitutive" promoters. A "constitutive" promoter is a promoter which is active under most environmental conditions.

A. Inducible Promoters

An inducible promoter is operably linked to a gene for expression in *petunia*. Optionally, the inducible promoter is operably linked to a nucleotide sequence encoding a signal sequence which is operably linked to a gene for expression in *petunia*. With an inducible promoter the rate of transcription increases in response to an inducing agent.

Any inducible promoter can be used in the instant invention. See Ward et al., *Plant Mol. Biol.* 22:361-366 (1993). Exemplary inducible promoters include, but are not limited to, that from the ACEI system which responds to copper (Meft et al., *PNAS* 90:4567-4571 (1993)); In2 gene from maize which responds to benzenesulfonamide herbicide safeners (Hershey et al., *Mol. Gen Genetics* 227:229-237 (1991) and Gatz et al., *Mol. Gen. Genetics* 243:32-38 (1994)) or Tet repressor from Tn10 (Gatz et al., Mol. Gen. Genetics 227:229-237 (1991)). A particularly preferred inducible promoter is a promoter that responds to an inducing agent to which plants do not normally respond. An exemplary inducible promoter is the inducible promoter from a steroid hormone gene, the transcriptional activity of which is induced by a glucocorticosteroid hormone (Schena et al., *Proc. Natl. Acad. Sci. U.S.A.* 88:0421 (1991)).

B. Constitutive Promoters

A constitutive promoter is operably linked to a gene for expression in *petunia* or the constitutive promoter is operably linked to a nucleotide sequence encoding a signal sequence which is operably linked to a gene for expression in *petunia*.

Many different constitutive promoters can be utilized in the instant invention. Exemplary constitutive promoters include, but are not limited to, the promoters from plant viruses such as the 35S promoter from CaMV (Odell et al., *Nature* 313:810-812 (1985), Tababeizadeh et al., *Plant Cell Report* 19:2 197-202 (1999), Kunik et al., *Acta Horticulturae* 447, 387-391 (1997)) and the promoters from such genes as rice actin (McElroy et al., *Plant Cell* 2:163-171 (1990)); ubiquitin (Christensen et al., *Plant Mol. Biol.* 12:619-632 (1989) and Christensen et al., *Plant Mol. Biol.* 18:675-689 (1992)); pEMU (Last et al., *Theor. Appl. Genet* 81:581-588 (1991)); MAS (Velten et al., *EMBO J.* 3:2723-2730 (1984)) and maize H3 histone (Lepetit et al., *Mol. Gen. Genetics* 231:276-285 (1992) and Atanassova et al., *Plant Journal* 2 (3): 291-300 (1992)).

The ALS promoter, Xba1/NcoI fragment, 5' to the *Brassica napus* ALS3 structural gene (or a nucleotide sequence similar to said Xba1/NcoI fragment), represents a particularly useful constitutive promoter. See PCT application WO96/30530.

C. Tissue-Specific or Tissue-Preferred Promoters

A tissue-specific promoter is operably linked to a gene for expression in *petunia*. Optionally, the tissue-specific promoter is operably linked to a nucleotide sequence encoding a signal sequence which is operably linked to a gene for expression in *petunia*. Plants transformed with a gene of interest operably linked to a tissue-specific promoter produce the protein product of the transgene exclusively, or preferentially, in a specific tissue.

Any tissue-specific or tissue-preferred promoter can be utilized in the instant invention. Exemplary tissue-specific or tissue-preferred promoters include, but are not limited to, a root-preferred promoter, such as that from the phaseolin gene (Murai et al., *Science* 23:476-482 (1983) and Sengupta-Gopalan et al., *Proc. Natl. Acad. Sci. U.S.A.* 82:3320-3324 (1985)), such as the promoter roID from *Agrobacterium rhizogenes* as mentioned in Grichko et al., *Plant Physiology and Biochemistry* 39:1 19-25 (2001); a leaf-specific and light-induced promoter such as that from cab or rubisco (Simpson et al., *EMBO J.* 4(11):2723-2729 (1985) and Timko et al., *Nature* 318:579-582 (1985)); an anther-specific promoter such as that from LAT52 (Twell et al., *Mol. Gen. Genetics* 217:240-245 (1989)); a pollen-specific promoter such as that from Zm13 (Guerrero et al., *Mol. Gen. Genetics* 244:161-168 (1993)) or a microspore-preferred promoter such as that from apg (Twell et al., *Sex. Plant Reprod.* 6:217-224 (1993)).

Signal Sequences for Targeting Proteins to Subcellular Compartments

Transport of protein produced by transgenes to a subcellular compartment such as the chloroplast, vacuole, peroxisome, glyoxysome, cell wall or mitochondrion or for secretion into the apoplast, is accomplished by means of operably linking the nucleotide sequence encoding a signal sequence to the 5' and/or 3' region of a gene encoding the protein of interest. Targeting sequences at the 5' and/or 3' end of the structural gene may determine, during protein synthesis and processing, where the encoded protein is ultimately compartmentalized.

The presence of a signal sequence directs a polypeptide to either an intracellular organelle or subcellular compartment or for secretion to the apoplast. Many signal sequences are known in the art. See, for example Becker et al., *Plant Mol. Biol.* 20:49 (1992); Close, P. S., Master's Thesis, Iowa State University (1993); Knox, C., et al., *Plant Mol. Biol.* 9:3-17 (1987); Lerner et al., *Plant Physiol.* 91:124-129 (1989); Fontes et al., *Plant Cell* 3:483-496 (1991); Matsuoka et al., *Proc. Natl. Acad. Sci.* 88:834 (1991); Gould et al., *J. Cell. Biol.* 108:1657 (1989); Creissen et al., *Plant J.* 2:129 (1991); Kalderon, et al., *Cell* 39:499-509 (1984); Steifel, et al., *Plant Cell* 2:785-793 (1990).

Methods for *Petunia* Transformation

Numerous methods for plant transformation have been developed including biological and physical plant transformation protocols. See, for example, Miki et al., "Procedures for Introducing Foreign DNA into Plants" in *Methods in Plant Molecular Biology and Biotechnology*, Glick B. R. and Thompson, J. E. Eds. (CRC Press, Inc., Boca Raton, 1993) pages 67-88. In addition, expression vectors and in vitro culture methods for plant cell or tissue transformation and regeneration of plants are available. See, for example, Gruber et al., "Vectors for Plant Transformation" in *Methods in Plant Molecular Biology and Biotechnology*, Glick B. R. and Thompson, J. E. Eds. (CRC Press, Inc., Boca Raton, 1993) pages 89-119.

A. *Agrobacterium*-Mediated Transformation

One method for introducing an expression vector into plants is based on the natural transformation system of *Agrobacterium*. See, for example, Frary et al., *Plant Cell Report*. 1996, 16: 3/4, 235-240, Roehel et al., *Plant Cell Report*. 1993, 12: 11, 644-647, Hu-Wei et al., *In Vitro Cellular and Devel-* opmental Biology Plant. 2001 37: 1, 12-18. *A. tumefaciens* and *A. rhizogenes* are plant pathogenic soil bacteria which genetically transform plant cells. The Ti and Ri plasmids of *A. tumefaciens* and *A. rhizogenes*, respectively, carry genes responsible for genetic transformation of the plant. See, for example, Kado, C. I., *Crit. Rev. Plant Sci.* 10:1 (1991). Descriptions of *Agrobacterium* vector systems and methods for *Agrobacterium*-mediated gene transfer are provided by Gruber et al., supra, Miki et al., supra, and Moloney et al., *Plant Cell Reports* 8:238 (1989). See also, U.S. Pat. No. 6,198,022 issued Mar. 6, 2001.

B. Direct Gene Transfer

Despite the fact the host range for *Agrobacterium*-mediated transformation is broad, some major cereal crop and vegetable species and gymnosperms have generally been recalcitrant to this mode of gene transfer, even though some success has recently been achieved in rice and corn. Hiei et al., *The Plant Journal* 6:271-282 (1994) and U.S. Pat. No. 5,591,616 issued Jan. 7, 1997. Several methods of plant transformation collectively referred to as direct gene transfer have been developed as an alternative to *Agrobacterium*-mediated transformation.

A generally applicable method of plant transformation is microprojectile-mediated transformation wherein DNA is carried on the surface of microprojectiles measuring 1 to 4 μm. The expression vector is introduced into plant tissues with a biolistic device that accelerates the microprojectiles to speeds of 300 to 600 m/s which is sufficient to penetrate plant cell walls and membranes. Sanford et al., *Part. Sci. Technol.* 5:27 (1987), Sanford, J. C., *Trends Biotech.* 6:299 (1988), Klein et al., *Bio/Technology* 6:559-563 (1988), Sanford, J. C., *Physiol Plant* 7:206 (1990), Klein et al., *Biotechnology* 10:268 (1992), Baum et al., *Plant Journal*. 1997, 12: 2, 463-469, Eck et al., *Plant Cell Report*. 1995, 14: 5, 299-304, Manzara et al., *Plant Molecular Biology Reporter* 123: 221-226 (1994).

Another method for physical delivery of DNA to plants is sonication of target cells. Zhang et al., *Bio/Technology* 9:996 (1991). Alternatively, liposome and spheroplast fusion have been used to introduce expression vectors into plants. Deshayes et al., *EMBO J.*, 4:2731 (1985), Christou et al., *Proc Natl. Acad. Sci. U.S.A.* 84:3962 (1987). Direct uptake of DNA into protoplasts using $CaCl_2$ precipitation, polyvinyl alcohol or poly-L-ornithine has also been reported. Hain et al., *Mol. Gen. Genet.* 199:161 (1985) and Draper et al., *Plant Cell Physiol.* 23:451 (1982). Electroporation of protoplasts and whole cells and tissues has also been described. Donn et al., In Abstracts of VIIth International Congress on Plant Cell and Tissue Culture IAPTC, A2-38, p 53 (1990), D'Halluin et al., *Plant Cell* 4:1495-1505 (1992) and Spencer et al., *Plant Mol. Biol.* 24:51-61 (1994). A transfer of chromosomes has been reported from a transformed donor line of potato to a recipient line of tomato through microprotoplast PEG induced fusion. See Ramalu et al., *Theorical and Applied Genetics* 92:316-325 (1996).

Following transformation of *petunia* target tissues, expression of the above-described selectable marker genes allows for preferential selection of transformed cells, tissues and/or plants, using regeneration and selection methods now well known in the art.

The foregoing methods for transformation would typically be used for producing a transgenic plant. The transgenic plant could then be crossed with another (non-transformed or transformed) plant in order to produce a new transgenic plant. Alternatively, a genetic trait which has been engineered into a particular *petunia* line using the foregoing transformation techniques could be moved into another line using traditional backcrossing techniques that are well known in the plant breeding arts. For example, a backcrossing approach could be used to move an engineered trait from a public, non-elite variety into an elite variety, or from a variety containing a foreign gene in its genome into a line which does not contain that gene. As used herein, "crossing" can refer to a simple X by Y cross, or the process of backcrossing, depending on the context.

Changes in plant phenotypes can be produced by inhibiting expression of one or more genes or by overexpressing one or more genes. Various promoters, targeting sequences, enhancing sequences, and other DNA sequences can be inserted into the *petunia* genome for the purpose of altering the expression of genes which results in altered flower color and/or altered flower color pattern similar to the flower color and/or flower color pattern produced by the mutant allele gc1-1 of the present invention.

Specifically inhibiting expression of one or more genes (also known as gene silencing, or gene suppression) can be accomplished by antisense inhibition or cosuppression (U.S. Pat. Nos. 5,190,931, 5,107,065 and 5,283,323). An antisense gene is a complete (full length) coding sequence of the gene of interest or a fragment thereof. An antisense gene may also be to an untranslated portion of an endogenous plant gene, such as a 5' untranslated leader region or a 3' untranslated terminator or polyadenylation region of the gene as it exists in plants. Expression of a transgenic antisense sequence allows for the regulation of the specific endogenous plant gene of interest. Antisense inhibition was first reported in electroporation of carrot protoplasts with antisense and sense constructs containing the CAT reporter gene resulted in varying inhibition of CAT activity dependent on promoter strength (Ecker et al., *Proc. Natl. Acad. Sci. U.S.A.* 83: 5372 5376, 1986). A stable inheritable antisense effect was first reported in tobacco using the NOS transgene (Rothstein et al., *Proc. Natl. Acad. Sci. U.S.A.* 84: 8439 8943, 1987). Constitutive expression of antisense chalcone synthase (CHS) in transgenic tobacco and *petunia* plants decreased endogenous CHS RNA and protein activity demonstrating the application of this technology in regulating endogenous gene expression (van der Krol et al., *Nature* 333: 866 869, 1988; van der Krol et al., Plant Molecular Biology 14: 457 466, 1990).

Many techniques for gene silencing are well known to one of skill in the art, including but not limited to knock-outs (such as by insertion of a transposable element such as mu (V. Chandler, The Maize Handbook, Springer-Verlag 1994) or other genetic elements such as a FRT, Lox or other site specific integration site, antisense technology (see, e.g., Sheehy et al. (1988) PNAS USA 85:8805 8809; and U.S. Pat. Nos. 5,107,065; 5,453,566; and 5,759,829); co-suppression (e.g., Taylor (1997) Plant Cell 9:1245; Jorgensen (1990) Trends Biotech. 8(12):340 344; Flavell (1994) PNAS USA 91:3490 3496; Finnegan et al. (1994) Bio/Technology 12: 883 888; and Neuhuber et al. (1994) Mol. Gen. Genet. 244:230 241); RNA interference (Napoli et al. (1990) Plant Cell 2:279 289; U.S. Pat. No. 5,034,323; Sharp (1999) Genes Dev. 13:139 141; Zamore et al. (2000) Cell 101:25 33; and Montgomery et al. (1998) PNAS USA 95:15502 15507), virus-induced gene silencing (Burton, et al. (2000) Plant Cell 12:691 705; and Baulcombe (1999) Curr. Op. Plant Bio. 2:109 113); target-RNA-specific ribozymes (Haseloff et al. (1988) Nature 334: 585 591); hairpin structures (Smith et al. (2000) Nature 407: 319 320; WO 99/53050; and WO 98/53083); MicroRNA (Aukerman & Sakai (2003) Plant Cell 15:2730 2741); ribozymes (Steinecke et al. (1992) *EMBO J.* 11:1525; and Perriman et al. (1993) Antisense Res. Dev. 3:253); oligonucleotide mediated targeted modification (e.g., WO 03/076574 and WO 99/25853); Zn-finger targeted molecules (e.g., WO 01/52620; WO 03/048345; and WO 00/42219); and other methods or combinations of the above methods known to those of skill in the art.

Overexpression of various genes in *petunia* which result in altered flower color and/or altered flower color pattern may be accomplished by first constructing a chimeric gene in which the coding region is operably linked to a promoter capable of directing expression of a gene in the desired tissues at the desired stage of development. The chimeric gene may comprise promoter sequences and translation leader sequences derived from the same genes. 3' Non-coding sequences encoding transcription termination signals may also be provided. The instant chimeric gene may also comprise one or more introns in order to facilitate gene expression.

Cosuppression, also known as cosense suppression, homology-dependent gene silencing, repeat-induced gene silencing, et cetera, is the inactivation of a gene in a cell where it is normally functional and may be used for altering flower color and/or altering flower color pattern in *petunia* (for reviews see Baulcombe et al., Current Opinion Biotechnol. 7: 173 180, 1996; Meyer et al., Annu. Rev. Plant Physiol. Plant Mol. Biol. 47: 23 48, 1996; Matzke et al., Plant Physiol. 107: 679 685, 1995). Transgene induced cosuppression in plants has been shown to have useful effects which include reduced impact of viral infection, fruit ripening, affecting flower color, inactivation of infecting transposons and retrotransposons, and editing aberrant RNA transcripts (Smyth et al., Current Biol. 7: 793 795, 1997; Napoli et al., Plant Cell 2: 279 289, 1990). Many examples of cosuppression have been reported in the literature: sense suppression of caffeic acid O-methyltransferase resulted in altered stem coloration of aspen (Tsai et al., Plant Physiology 117: 101 112, 1998); cosuppression of a lipoxygenase isozyme (LOX2) resulted in transgenic *Arabidopsis* plants unable to accumulate jasmonic acid following wounding (Bell et al., Proc. Natl. Acad. Sci. U.S.A. 92: 8675 8679, 1995); cosuppression of phytochrome-regulated chlorophyll .alpha./.beta. 140 RNA levels in *Arabidopsis* (Brussian et al., Plant Cell 5: 667 677, 1993); cosuppression of a pea cDNA encoding light-activated chloroplast NADP-malate dehydrogenase in transgenic tobacco (Faske et al., Plant Physiol. 115: 705 715, 1997); cosuppression of Flaveria bidentis NADP-MDH via heterologous sorghum NADP-MDH cDNA despite only about 71% sequence homology (Trevanion et al., Plant Physiol. 113: 1153 1163, 1997); cosuppression of a proline-rich glycoprotein (TTS) involved in pollen tube growth in transgenic tobacco (Cheung et al., Cell 82: 383 393, 1995); cosuppression of phenylalanine ammonia-lyase (PAL) in transgenic tobacco (Elkind et al., Proc. Natl. Acad. Sci. U.S.A. 87: 9057 9061); and cosuppression of two MADS box floral binding protein genes (FBP7 and FBP11) in *petunia* (Colombo et al., Plant Cell 9: 703 715, 1997).

DEPOSIT INFORMATION

*Petunia* seeds containing the gc1-1 mutant allele have been placed on deposit under the Budapest Treaty with the American Type Culture Collection (ATCC), 10801 University Boulevard, Manassas, Va. 20110-2209 on Dec. 19, 2006 and having Deposit Accession Number PTA-8092. Access to this deposit will be available during the pendency of this application to persons determined by the Commissioner of Patents and Trademarks to be entitled thereto under 37 CFR § 1.14 and 35 USC § 122. Upon allowance of any claims in this application, all restrictions on the availability to the public of the seeds containing the gc1-1 mutant allele will be irrevocably removed by affording access to the deposit of at least 2,500 seeds of the same seeds on deposit with the American Type Culture Collection, Manassas, Va. The deposit will be maintained in the depository for a period of 30 years, or 5 years after the last request, or for the effective life of the patent, whichever is longer, and will be replaced as necessary during that period.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

What is claimed is:

1. A *petunia* seed containing an allele designated gc1-1 wherein a representative sample of seed containing said gc1-1 allele has been deposited under ATCC Accession No. PTA-8092.

2. A *petunia* seed containing a dominant allele designated gc1-1 for altered flower color and/or altered flower color pattern wherein a representative sample of said seed containing said gc1-1 allele has been deposited under ATCC Accession No. PTA-8092.

3. A *petunia* plant, or a part thereof, produced by growing the seed of claim 1.

4. A tissue culture of cells produced from the plant of claim 3, wherein said cells of the tissue culture are produced from a plant part selected from the group consisting of leaf, pollen, embryo, cotyledon, hypocotyl, meristematic cell, root, root tip, pistil, anther, flower, stem, and petiole.

5. A protoplast produced from the plant of claim 3.

6. A protoplast produced from the tissue culture of claim 4.

7. A *petunia* plant regenerated from said tissue culture of claim 4.

8. A method for producing hybrid *petunia* seed comprising crossing a first parent *petunia* plant with a second *parent* petunia plant and harvesting the resultant hybrid *petunia* seed, wherein first and/or second parent petunia plant is the petunia plant of claim 3.

9. A hybrid *petunia* plant produced by growing said hybrid *petunia* seed of claim 8.

10. A *petunia* plant produced by growing the seed of claim 2.

11. A tissue culture of cells produced from the plant of claim 10, wherein said cells of the tissue culture are produced from a plant part selected from the group consisting of leaf, pollen, embryo, cotyledon, hypocotyl, meristematic cell, root, root tip, pistil, anther, flower, stem, and petiole.

12. A protoplast produced from the plant of claim 10.

13. A protoplast produced from the tissue culture of claim 11.

14. A *petunia* plant regenerated from said tissue culture of claim 11.

15. A method for producing hybrid *petunia* seed comprising crossing a first parent *petunia* plant with a second parent *petunia* plant and harvesting the resultant hybrid *petunia* seed, wherein said first and/or second parent *petunia* plant is the *petunia* plant of claim 10.

16. A hybrid *petunia* plant produced by growing said hybrid *petunia* seed of claim 15.

17. A method for producing a *Calibrachoa-petunia* plant comprising crossing a *Calibrachoa* plant with the *petunia* plant of claim 3, harvesting the resultant hybrid embryo and regenerating a *Calibrachoa-petunia* plant from said hybrid embryo.

18. A *Calibrachoa-petunia* plant produced by the method of claim 17.

19. A tissue culture of cells produced from the plant of claim 18, wherein said cells of the tissue culture are produced from a plant part selected from the group consisting of leaf, pollen, embryo, cotyledon, hypocotyl, meristematic cell, root, root tip, pistil, anther, flower, stem, and petiole.

20. A protoplast produced from the plant of claim 18.

21. A protoplast produced from the tissue culture of claim 19.

22. A *Calibrachoa-petunia* plant regenerated from said tissue culture of claim 19.

23. A method for producing an ornamental plant comprising crossing an ornamental plant with the *petunia* plant of claim 3, harvesting the resultant hybrid embryo and regenerating an ornamental plant from said hybrid embryo.

24. A method for producing ornamental plant seed comprising crossing an ornamental plant with the *petunia* plant of claim 3 and harvesting the resultant seed.

* * * * *